(12) United States Patent
Berler et al.

(10) Patent No.: US 10,980,950 B2
(45) Date of Patent: Apr. 20, 2021

(54) ULTRA-LOW WASTE NEEDLE AND SYRINGE SYSTEM THAT AUTOMATICALLY AND PASSIVELY RENDERS A NEEDLE SAFE DURING THE INJECTION PROCESS

(71) Applicant: Sharps Technology Inc., New York, NY (US)

(72) Inventors: Barry Berler, Huntingdon Valley, PA (US); Anthony F. Mulone, Jr., Marstons Mills, MA (US); Kevin Corely, Waltham, MA (US); Niv Yaari, Rosh HaAyin (IL); Gil Katz, Avtalyon (IL); Gregory Udovich, Haifa (IL)

(73) Assignee: Sharps Technology Inc., New York, NY (US)

( * ) Notice: Subject to any disclaimer, the term of this patent is extended or adjusted under 35 U.S.C. 154(b) by 0 days.

(21) Appl. No.: 16/660,796

(22) Filed: Oct. 22, 2019

(65) Prior Publication Data

US 2020/0129708 A1 Apr. 30, 2020

Related U.S. Application Data

(60) Provisional application No. 62/750,803, filed on Oct. 25, 2018.

(51) Int. Cl.
*A61M 5/32* (2006.01)
*A61M 5/31* (2006.01)
*A61M 5/20* (2006.01)

(52) U.S. Cl.
CPC ........ *A61M 5/3269* (2013.01); *A61M 5/3129* (2013.01); *A61M 2005/2073* (2013.01)

(58) Field of Classification Search
CPC .. A61M 5/3269; A61M 5/326; A61M 5/3129; A61M 2005/3265;
(Continued)

(56) References Cited

U.S. PATENT DOCUMENTS

| 4,559,043 | A | 12/1985 | Whitehouse et al. |
| 5,104,384 | A | 4/1992 | Parry |

(Continued)

FOREIGN PATENT DOCUMENTS

CA 2236049 7/2006

*Primary Examiner* — Tiffany Legette
*Assistant Examiner* — Alexandra Lalonde
(74) *Attorney, Agent, or Firm* — LaMorte & Associates P.C.

(57) ABSTRACT

A needle and syringe system that provides ultra-low dosage waste and automatic needlestick protection. A syringe assembly is provided that contains a barrel and a plunger. A tubular spacer is disposed in the barrel. A needle head assembly is provided that includes a collar and a needle. A safety slide is positioned between the needle and the collar. The safety slide has a sheathing tube that surrounds part of the needle. The safety slide can move relative the needle. In a first position, the sheathing tube does not extend beyond the sharpened end of the needle. In a second position, the sheathing tube extends beyond the sharpened end of the needle. When advanced, the plunger head moves the tubular spacer. The tubular spacer passes over the base of the needle and presses against the safety slide. The safety slide is moved from the first position to the second position.

16 Claims, 6 Drawing Sheets

(58) Field of Classification Search
CPC ........ A61M 2005/2073; A61M 5/3243; A61M 5/321; A61M 5/3205; A61M 5/32; A61M 5/31; A61M 5/178
See application file for complete search history.

(56) References Cited

U.S. PATENT DOCUMENTS

| | | |
|---|---|---|
| 5,306,258 A | 4/1994 | de la Fuente |
| 5,314,503 A | 5/1994 | Bobrove et al. |
| 5,370,628 A | 12/1994 | Allison et al. |
| 5,385,555 A | 1/1995 | Hausser |
| 5,460,611 A | 10/1995 | Alexander |
| 5,733,264 A | 3/1998 | Flowers |
| 5,891,092 A | 4/1999 | Castellano |
| 5,902,270 A | 5/1999 | Jentzen |
| 6,616,636 B2 | 9/2003 | Lee |
| 6,626,863 B1 | 9/2003 | Berler |
| 2004/0162530 A1* | 8/2004 | Kirk ................. A61M 5/32 604/240 |
| 2007/0016140 A1 | 1/2007 | Berler |
| 2007/0016145 A1 | 1/2007 | Berler |
| 2008/0009808 A1 | 1/2008 | Berler |
| 2008/0097337 A1 | 4/2008 | Judd et al. |
| 2008/0319346 A1 | 12/2008 | Crawford et al. |
| 2011/0257603 A1* | 10/2011 | Ruan ................. A61M 5/326 604/198 |
| 2016/0367764 A1 | 12/2016 | Doyle |
| 2017/0319791 A1 | 11/2017 | Giambattista et al. |

* cited by examiner

ULTRA-LOW WASTE NEEDLE AND SYRINGE SYSTEM THAT AUTOMATICALLY AND PASSIVELY RENDERS A NEEDLE SAFE DURING THE INJECTION PROCESS

RELATED APPLICATIONS

This application claims the benefit of U.S. provisional patent application No. 62/750,803, filed Oct. 25, 2018.

BACKGROUND OF THE INVENTION

1. Field of the Invention

In general, the present invention relates to syringes that are used to make injections through a needle or cannula. More particularly, the present invention relates to safety syringes where the needle automatically becomes shielded after use.

2. Prior Art Description

Millions of injections are performed in the United States of America each year. The injections are typically performed using a hypodermic needle and a syringe. The length of the hypodermic needle and the gauge of the needle depend upon the application and whether the injection is intramuscular, subcutaneous, intravenous, or intradermal. The compounds being injected also vary widely. Some injection materials, such as saline, are very inexpensive. However, many pharmaceutical compounds, such as certain gene therapy compounds, can cost tens of thousands of dollars per injection. As such, a fraction of a milliliter of the pharmaceutical can be worth hundreds of dollars.

When a traditional hypodermic needle and syringe are used to perform an injection, there is inevitably some volume of injection material that remains within the needle and syringe after the injection is complete. The pharmaceutical material remaining is thrown away with the needle and syringe after the injection. The amount of injection material remaining within the needle and syringe depends upon the design of the needle and syringe. With some injection material, injection as small as 50 microliters may be performed. This volume is near the dead space volume of many prior art needle and syringe designs. As a result, in order make an injection of 50 microliters, over 100 microliters must be drawn into the needle and syringe. The result is that half of the injection material drawn into the needle and syringe are thrown away. The pharmaceutical material retained in the dead space of inefficient needle and syringe designs adds up to billions of dollars in wasted pharmaceuticals, when all injections are considered.

In the prior art, thought is rarely given to the volume of residual material that inherently remains within a hypodermic syringe and needle. Some needle and syringe assemblies have been designed where a syringe plunger and a needle head make flush contact. Such prior art designs are exemplifed by U.S. Pat. No. 6,616,636 to Lee and U.S. Pat. No. 5,902,270 to Jentzen. However, in a real healthcare environment, such as a hospital, different syringes are used with many different needle heads, depending upon the specific medical application. Some needle head and syringe combinations are efficient in the discharge of pharmaceutical compounds and some are not.

The problem becomes more complicated when a needle head and syringe are part of a safety syringe assembly. Safety syringe assemblies are designed to both perform an injection and to provide some mechanism for minimizing the likelihood of a needlestick injury. Needlestick injuries are commonplace among healthcare workers. Needlestick injuries are defined by the United States National Institute of Occupational Safety and Health as injuries caused by needles such as hypodermic needles, blood collection needles, intravenous (IV) stylets, and needles used to connect parts of IV delivery systems. Needlestick injuries can transfer blood-borne pathogens such as Hepatitis B virus, Hepatitis C virus, and Human Immunodeficiency Virus (HIV). For healthcare workers, needle stick injuries are responsible for a significant proportion of these diseases in the healthcare workforce.

It has been estimated by the Center for Disease Control, that in the United States of America, more than three million healthcare workers are exposed to blood and body fluids via needle mishaps each year. Most healthcare workers are trained with procedures for using and disposing of used needles. Used needles should not be recapped, in order to prevent the potential for needlestick injuries. However, many studies have revealed that recapping is still prevalent among healthcare workers.

In an attempt to reduce the number of needlestick injuries, various safety needles have been developed that act to cover a needle the instant the needle is retracted from the skin. This is typically accomplished by advancing a tubular sheath along the shaft of the needle until the sheath covers the tip of the needle. Such prior art is exemplified by U.S. Pat. No. 6,626,863 to Berler, U.S. Patent Application Publication No. 2007/0016140 to Berler, U.S. Patent Application Publication No. 2007/0016145 to Berler, and U.S. Patent Application Publication No. 2008/0009808 to Berler. However, integrating a safety mechanism within a needle head typically takes additional room within the needle head. More room used in the needle head means that there is more dead space in the needle head where residual pharmaceutical compounds can collect. As a consequence, there are often opposing concerns that must be balanced in a design. The safety features of a design are balanced with the wasted pharmaceutical retained because of the safety features.

The use of safety syringes also often requires a change in injection technique. That is, the healthcare worker must alter the manner in which they use the needle and syringe in order to activate the safety feature. This often requires the healthcare worker to use two hands and to grasp the needle and syringe near the needle after use. The activation of the safety system is not automatic and leaves a healthcare worker vulnerable to needlestick injuries while attempting to activate the safety system.

A need therefore exists for an improved hypodermic needle and syringe assembly where the needle is automatically shielded after an injection and wherein the assembly does not retain any significant volume of the material being injected.

A need exists for a safety needle and syringe system that can be operated with one hand using the same techniques as traditional needle and syringe systems.

Lastly, a need exists for a safety needle and syringe system that automatically activates and prevents access to the needle tip even before the needle is withdrawn from a patient.

These needs are met by the present invention as described and claimed below.

SUMMARY OF THE INVENTION

The present invention is a needle and syringe system that provides ultra-low dosage waste and automatic needlestick protection with one-handed operation. A syringe assembly is provided that contains a barrel and a plunger. The plunger has a plunger head that moves in the barrel. A tubular spacer is disposed in the barrel near is its top end. The spacer has a central opening so that an injection compound can flow through the spacer.

A needle head assembly is provided that selectively attaches to the open end of the barrel. The needle head assembly includes a collar for engaging the barrel and a needle with a sharpened first end.

A safety slide is positioned between the needle and the collar within the needle head assembly. The safety slide has a sheathing tube that surrounds part of the needle. The safety slide can move relative the needle between a first position and a second position. In the first position, the sheathing tube does not extend beyond the sharpened first end of the needle. In the second position, the sheathing tube extends beyond the sharpened first end of the needle and prevents needle-sticks.

When the plunger is advanced in the barrel, the tubular spacer begins to move due to the increased pressure within the plunger barrel. Eventually, the plunger head contacts the tubular spacer and move it to its furthest position in the assembly. The tubular spacer passes over the base of the needle and presses against the safety slide. The safety slide is moved by the tubular spacer from the first position to the second position as the injection is performed. As the safety slide is advanced, the sheathing tube extends over the sharpened end of the needle. This occurs during the injection, therein protecting the tip of the needle even before the needle is withdrawn from a patient.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

The present invention needle and syringe system can be configured in many ways and can be adapted for use in many applications. However, only one exemplary embodiment is selected for the purposes of description and illustration. The illustrated embodiment, however, is merely exemplary and should not be considered a limitation when interpreting the scope of the appended claims.

Figure 1:
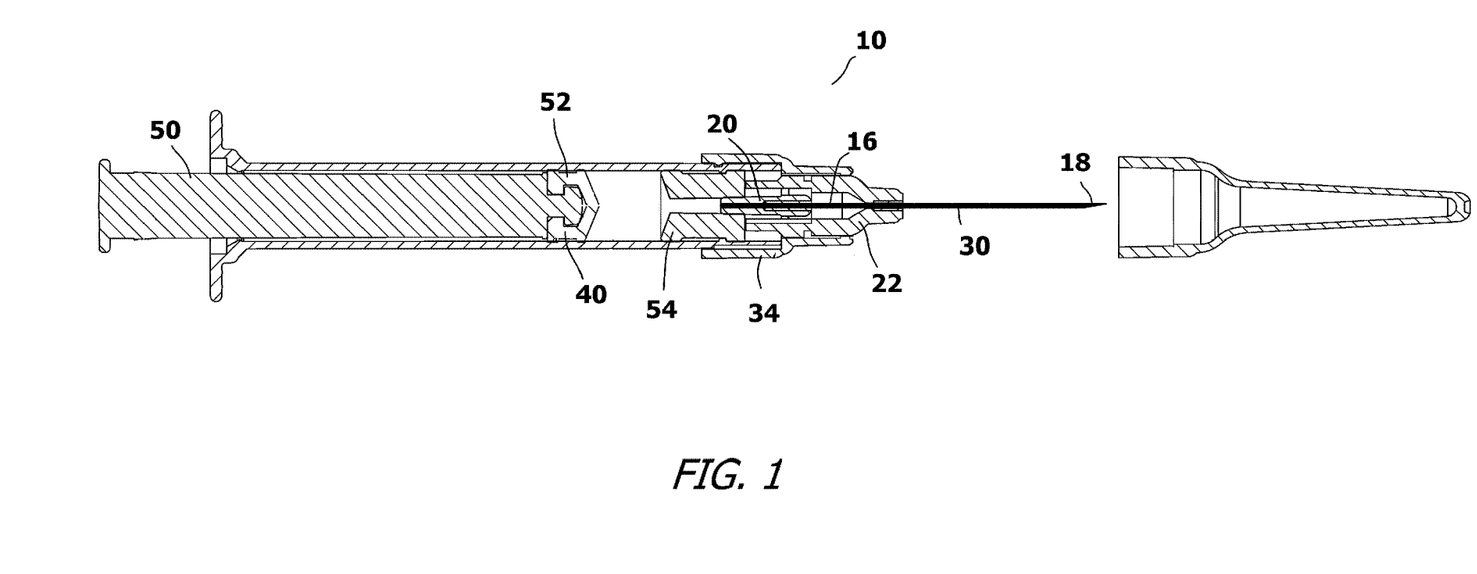
FIG. 1 is a cross-sectional view of an exemplary embodiment of safety needle and syringe system that contains a syringe assembly attached to a needle head assembly.
Figure 2:
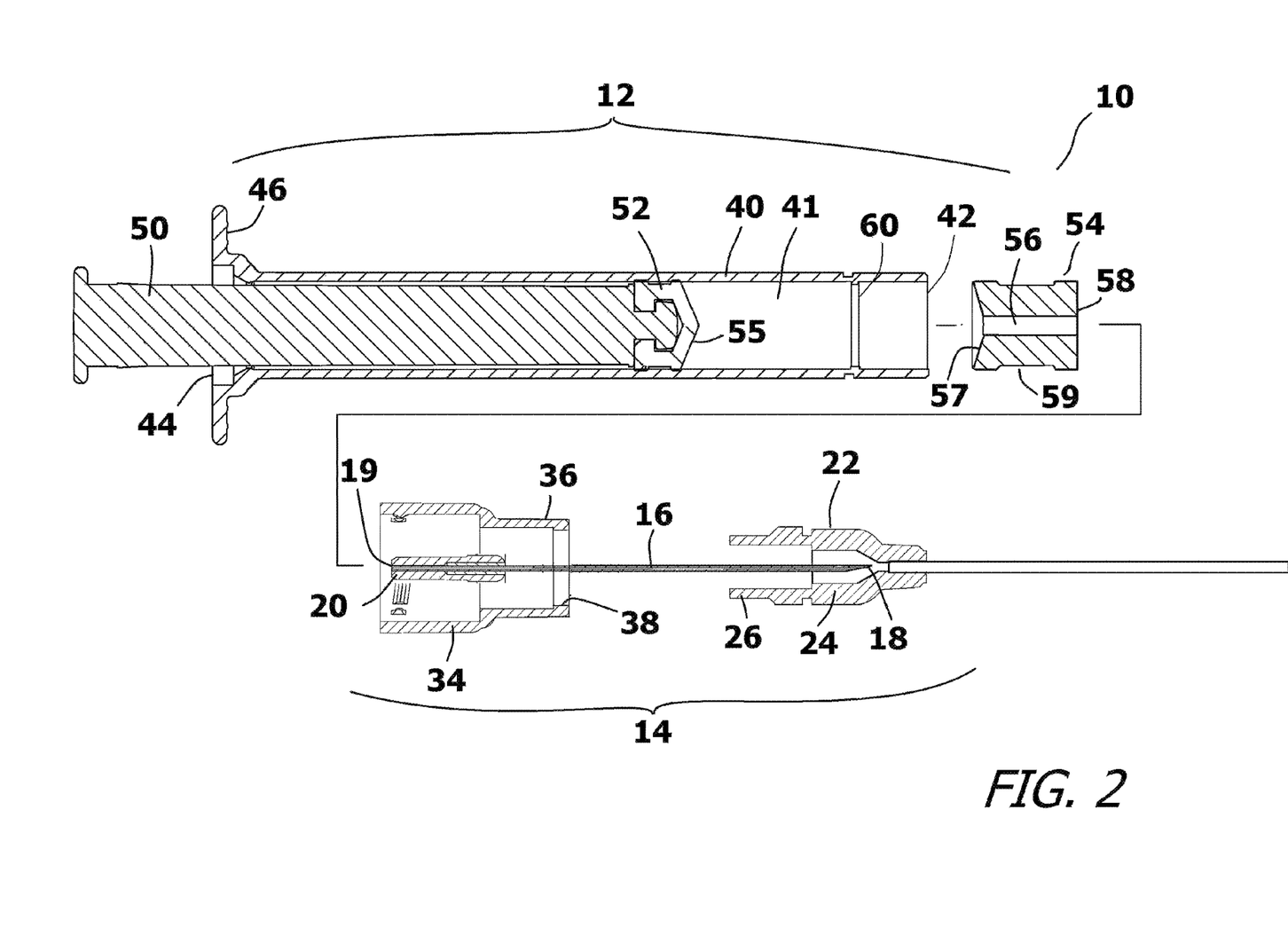
FIG. 2 shows an exploded view of the exemplary embodiment of FIG. 1.

Referring to FIG. 1 and FIG. 2, the present invention needle and syringe system 10 is shown. In the shown embodiment, the needle and syringe system 10 includes two primary assemblies that are selectively joined by a healthcare professional just prior to use. The primary assemblies include a syringe assembly 12 and a needle head assembly 14.

The needle head assembly 14 includes a needle 16. The needle 16 has a sharpened first end 18 and an opposite second end 19. The gauge of the needle 16 and the length of the needle 16 are selected by the healthcare professional for the medical procedure being performed. Within the needle head assembly 14, part of the needle 16 is set into an elongated base 20. The elongated base 20 is tubular and does not obstruct flow through the needle 16. As such, the needle 16 and the elongated base 20 move together as a single unit.

Figure 3:
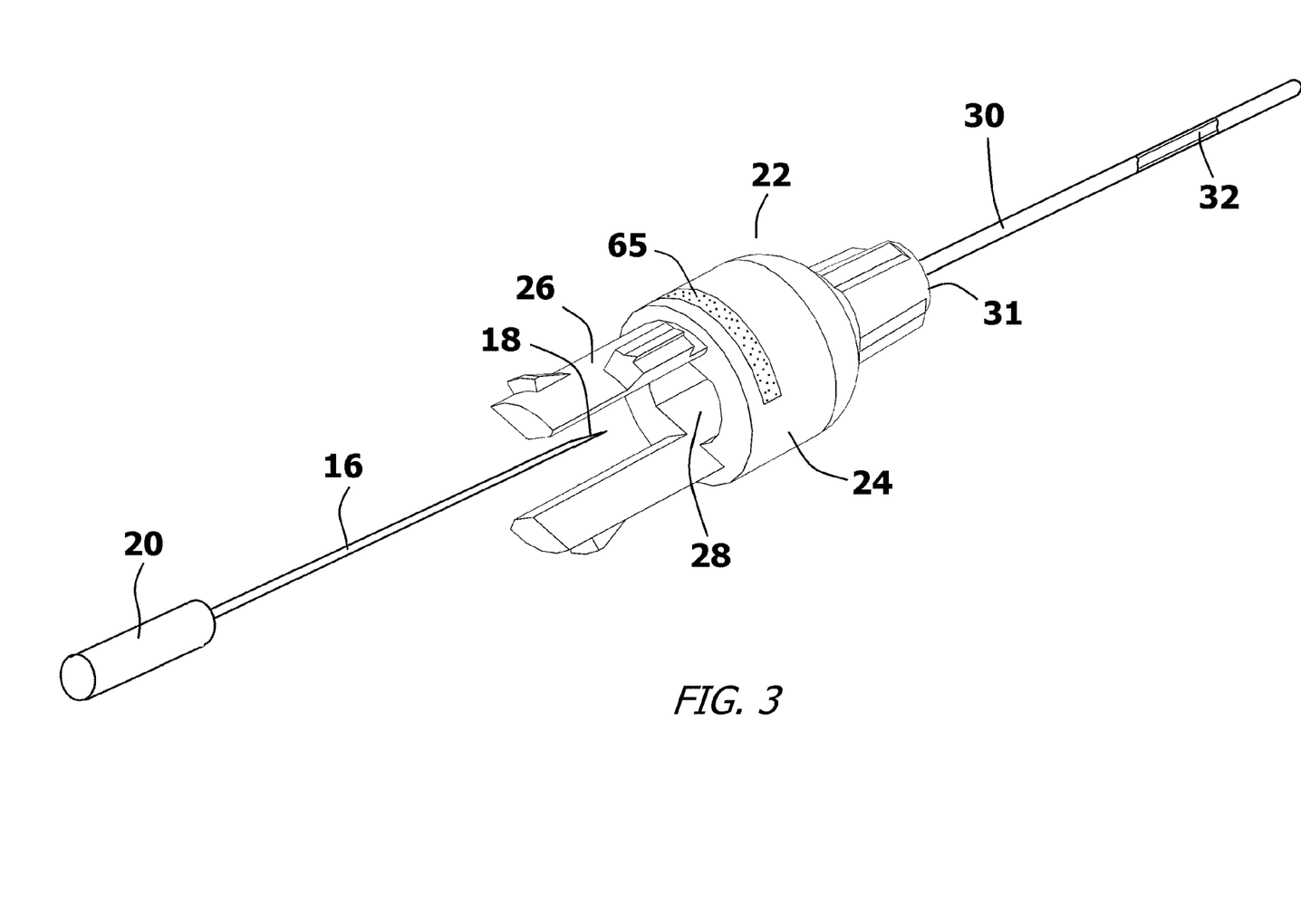
FIG. 3 shows a perspective view of the safety slide component of the needle head assembly.

Referring to FIG. 3, in conjunction with FIG. 2, it can be seen that the needle 16 is selectively protected by the relative movement of a safety slide 22. The safety slide 22 has a tubular body 24. Legs 26 extend from a first end 27 of the tubular body 24. The tubular body 24 defines a central cavity 28 that is sized to receive the elongated base 20 of the needle 16. A sheathing tube 30 extends from a second end 31 of the safety slide 22 opposite the legs 26. The extending sheathing tube 30 is cantilevered and defines a conduit 32 that communicates with the central cavity 28. The elongated base 20 extends into the central cavity 28 of the safety slide 22 and the needle 16 extends through the sheathing tube 30 of the safety slide 22. As will be explained, the safety slide 22 is able to move relative the needle 16 and the elongated base 20.

Figure 4:
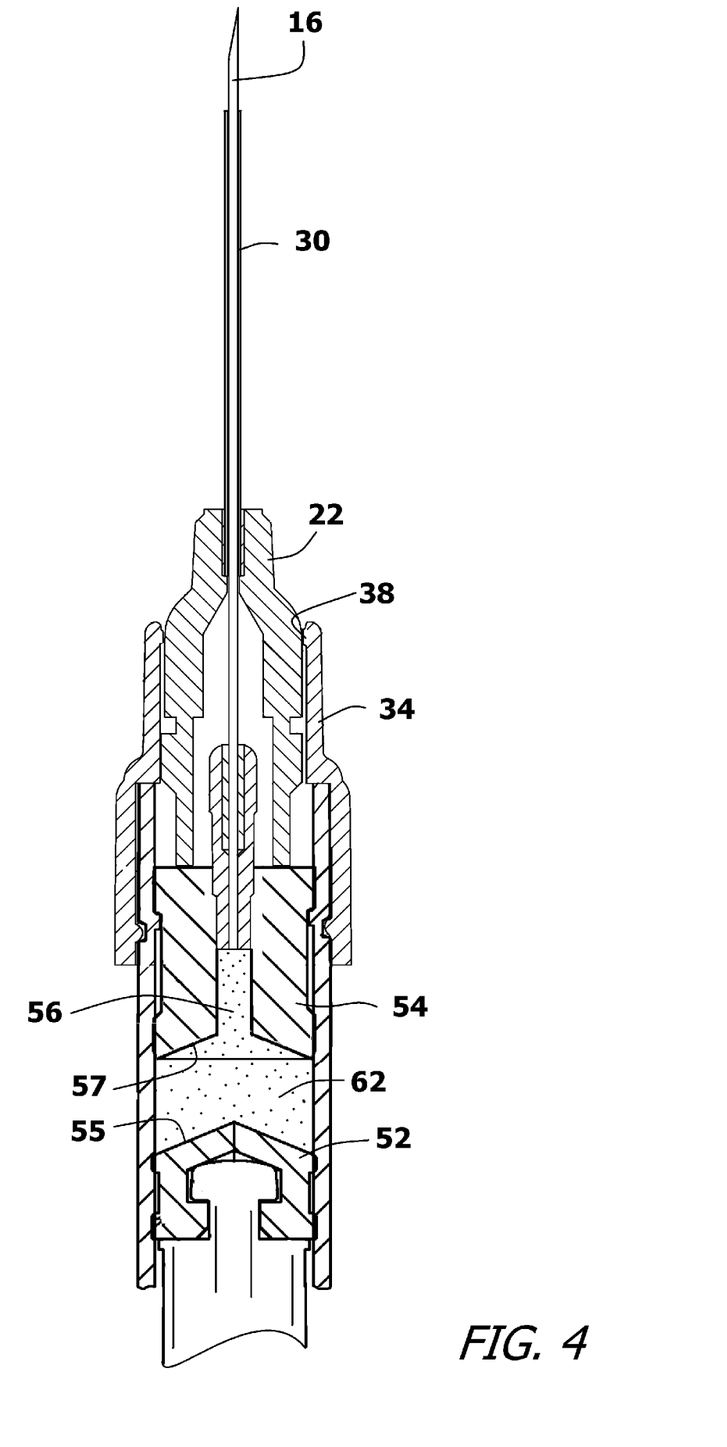
FIG. 4 is an enlarged cross-sectional view of the neck of the syringe assembly and the needle head assembly prior to the activation of the safety slide in the needle head assembly.

Referring to FIG. 2 in conjunction with FIG. 4, FIG. 5 and FIG. 6, it will be explained that prior to use (FIG. 4), the safety slide 22 is retracted and the needle 16 extends beyond the sheathing tube 30 where it can be used. During use (FIG. 5), the safety slide 22 extends the sheathing tube 30 along the needle 16. After use, (FIG. 6) the safety slide 22 extends the sheathing tube 30 so that it covers all of the needle 16, therein rendering the needle 16 safe.

The needle head assembly 14 includes a collar 34 that surrounds the safety slide 22. The collar 34 mechanically attaches to the syringe assembly 12 with a bayonet connection, a threaded connection, or a similar mechanical connection. As such, the collar 34 is used to interconnect the needle head assembly 14 to the syringe assembly 12. The collar 34 has a tapered neck 36 that abuts against the safety slide 22 and guides movement of the safety slide 22 during operation. One or more locking protrusions 38 are formed on the interior of the tapered neck 36. The locking protrusions 38 are biased against the safety slide 22 for a purpose that is later described.

The syringe assembly 12 has a barrel 40. The barrel 40 defines a tubular chamber 41 that extends between an open first end 42 and an open second end 44. The tubular chamber 41 is uniform between the open first end 42 and the open second end 44 with the exception of a ring protrusion 60 formed a short distance from the open first end 42. The exterior of the barrel 40 near the first end 42 is threaded or otherwise configured to be engaged by the collar 34 of the needle head assembly 14. Likewise, the exterior of the barrel 40 at the opposite second end 44 has finger flanges 46, to facilitate the proper gripping of the overall needle and syringe system 10.

A plunger 50 is set within the barrel 40. The plunger 50 has a plunger head 52 that seals against the tubular chamber 41 within the barrel 40 as the plunger 50 reciprocally moves within the barrel 40. The plunger head 52 has a face surface 55 that faces the open first end 42 of the barrel 40.

A tubular spacer 54 is positioned within the tubular chamber 41 of the barrel 40. The tubular spacer 54 has a central opening 56 that extends between a first end 57 and a second end 58. The first end 57 of the tubular spacer 54 is oriented toward the face surface 55 of the plunger head 52 and is configured to abut against the plunger head 52 with no intervening gap spaces. The central opening 56 in the tubular spacer 54 is sized to receive the elongated base 20 at the bottom of the needle 16. The tubular spacer 54 is sized to fit within the tubular chamber 41 of the barrel 40. The tubular spacer 54 has a recessed area 59 on its exterior that is engaged by the ring protrusion 60 on the interior of the tubular chamber 41. The presence of the ring protrusion 60 within the recessed area 59 limits the range of reciprocal movement for the tubular spacer 54 within the barrel 40.

It will be understood that in order to utilize the needle and syringe system 10, a needle head assembly 14 and a syringe assembly 12 are selected that are appropriate for the medical injection to be performed. The needle head assembly 14 is manually attached to the syringe assembly 12. A precise volume of injection compound 62 is then drawn into the needle and syringe system 10 in the traditional manner by retracting the plunger 50 within the barrel 40.

Before use, the sharpened first end 18 of the needle 16 is exposed. The first end 18 of the needle 16 is used to make an injection through a patient's skin. Due to the fineness of the sheathing tube 30, the sheathing tube 30 also typically passes into the skin through the opening made by the needle 16. The compound is injected by advancing the plunger head 52 toward the needle head assembly 14. As is indicated by FIG. 4, FIG. 5 and FIG. 6 in sequence, the needle 16 and the elongated base 20 remain stationary before, during and after an injection. The elongated base 20 partially extends into the central opening 56 of the tubular spacer 54. In this manner, the injection compound 62 that flows through the needle 16 can freely flow through the tubular spacer 54. When the injection compound 62 is drawn into the barrel 40, the tubular spacer 54 is held in place by the ring protrusion 60 in the barrel 40 interacting with the recessed area 59 on the tubular spacer 54.

As the plunger 50 advances in the barrel 40, the injection compound 62 is displaced out of the barrel 40 through the needle 16. During the injection, the movement of the plunger 50 increases the pressure of the injection compound 62. The injection compound 62 presses against the tubular spacer 54 and begins to move the tubular spacer 54 forward as the injection is taking place. Referring to FIG. 5, it can be seen that when the plunger head 52 initially contacts the tubular spacer 54, there are no gap spaces between the plunger head 52 and the tubular spacer 54. The only areas that contain the injection compound 62 is inside the needle 16 and in the central opening 56 of the tubular spacer 54 that is not occupied by the elongated base 20 of the needle 16. However, at this point, the plunger 50 is not yet fully depressed within the barrel 40.

Figure 6:
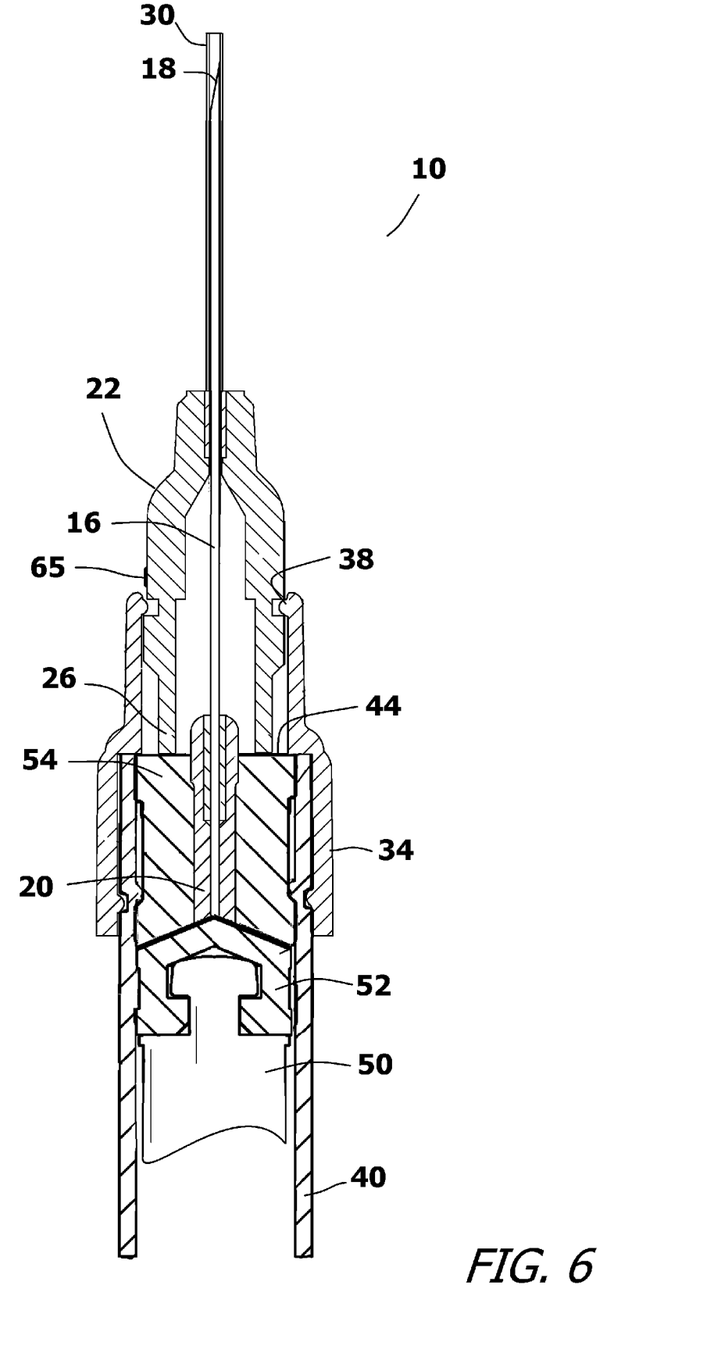
FIG. 6 is an enlarged cross-sectional view of the neck of the syringe assembly and the needle head assembly after to the activation of the safety slide in the needle head assembly.

Referring to FIG. 6, it can be seen that as the plunger 50 is advanced fully, the plunger head 52 contacts and pushes the tubular spacer 54 to the open second end 44 of the barrel 40. At this point, the plunger head 52 contacts the elongated base 20 of the needle 16. As a consequence, there is no more open space within the tubular spacer 54. The only place where the injection compound 62 can remain is within the needle 16 itself. This area is very small and is much less than 1% of the volume of the injection compound 62 initially held by the needle and syringe assembly 10. It will therefore be understood, that the injection compound 62 retained by the needle and syringe assembly 10 after a completed injection is de minimis.

Figure 5:
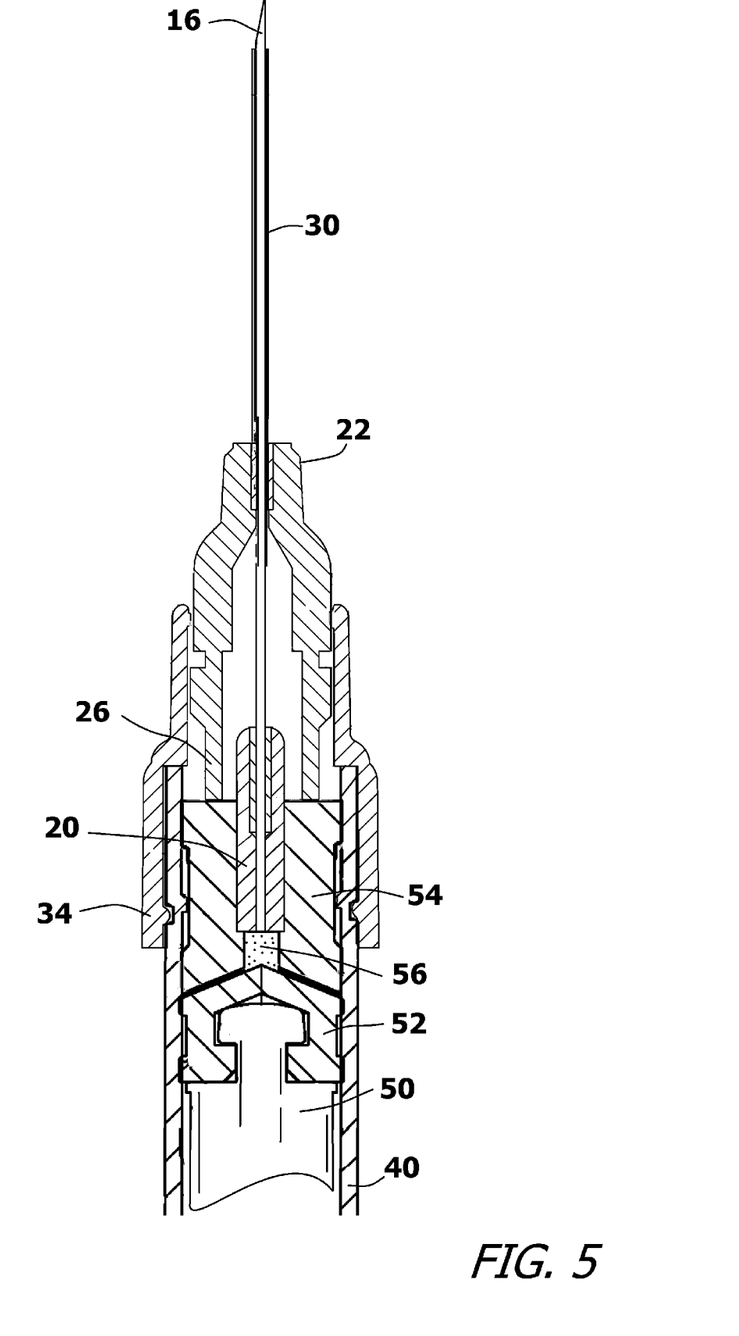
FIG. 5 is an enlarged cross-sectional view of the neck of the syringe assembly and the needle head assembly during the activation of the safety slide in the needle head assembly.

Referring to both FIG. 5 and FIG. 6 in conjunction with FIG. 3, it will be understood that as the tubular spacer 54 is advanced toward the second end 44 of the barrel 40 by the plunger head 52, the increased pressure within the barrel 40 moves the tubular spacer 54 forward. Eventually, the tubular spacer 54 presses against the legs 26 of the safety slide 22 and continues to move the safety slide 22 forward. As a consequence, the safety slide 22 is moved forward during the injection procedure. As the safety slide 22 moves forward, the sheathing tube 30 is advanced over the needle 16, wherein the sheathing tube 30 eventually extends beyond the sharpened first end 18 of the needle 16. This renders the needle 16 safe. The sheathing tube 30 moves with the safety slide 22 during the injection procedure. The sheathing tube 30 passes into the patient as it advances along the needle 16. The sheathing tube 30 extends beyond the needle 16 before the injection process is complete. As such, when the needle 16 is withdrawn from a patient, the needle 16 is already protected by the sheathing tube 30.

As the safety slide 22 advances within the stationary collar 34, the locking protrusions 38 on the collar 34 engage the safety slide 22 and locks the safety slide 22 into place. This prevents the needle head assembly 14 from being reset and reused. Additionally, as the safety slide 22 advances within the collar 34, a visual indicator 65 (FIG. 3) on the exterior of the safety slide 22 becomes visible. The visual indicator 65 becomes visible as the safety slide 22 locks in engagement with the collar 34. The visual indicator 65 enables a healthcare worker to see that the needle and syringe system 10 has been used and that the system 10 is locked into a safe configuration and is ready for disposal.

It will be understood that the embodiment of the present invention that is illustrated and described is merely exemplary and that a person skilled in the art can make many variations to that embodiment. For example, there are many locking devices that can be utilized between the collar and the safety slide to lock these elements together at the completion of an injection. All such embodiments are intended to be included within the scope of the present invention as defined by the claims.

What is claimed is:

1. A needle and syringe system, comprising:
    a syringe barrel having a first open end, wherein said syringe barrel defines a tubular chamber accessible through said first open end;
    a ring protrusion extending inwardly from said syringe barrel into said tubular chamber;
    a plunger with a plunger head that can be reciprocally moved within said syringe barrel, wherein said plunger head has a face surface that faces said first open end of said syringe barrel;
    a spacer disposed in said syringe barrel, said spacer having an exterior with a recessed area disposed along said exterior, a central opening that extends through said spacer, and a contact surface that faces said face surface of said plunger head, wherein said ring protrusion on said syringe barrel extends into said recessed area of said spacer and limits reciprocal movement of said spacer within said syringe barrel;
    a collar that selectively connects to said syringe barrel, wherein said collar supports a needle base that extends into said central opening of said spacer;

a needle that extends between a sharpened first end and an opposite second end, wherein said needle is affixed to said needle base;

a safety slide extending from said collar, wherein said safety slide has a sheathing tube extending therethrough that surrounds part of said needle, and wherein said safety slide can move relative to said needle and said collar between a first position, where said sheathing tube does not extend beyond said sharpened first end of said needle, and a second position where said sheathing tube extends beyond said sharpened first end of said needle;

wherein said plunger can move in said syringe barrel and cause said plunger head to contact and move said spacer, wherein said spacer advances over said needle base, and said safety slide moves from said first position to said second position.

2. The system according to claim 1, wherein said needle base moves through said central opening in said spacer to said contact surface of said spacer as said safety slide moves from said first position to said second position.

3. The system according to claim 1, wherein said contact surface of said spacer and said face surface of said plunger head conform so that no spaces exist between said contact surface and said face surface upon contact between said contact surface and said face surface.

4. The system according to claim 1, further including a lock that automatically locks said safety slide in said second position as said safety slide enters said second position.

5. The system according to claim 1, further including a visual indicator on said safety slide that becomes visible when said safety slide enters said second position.

6. The system according to claim 1, wherein said syringe barrel mechanically engages said spacer and limits movement of said spacer within said syringe barrel to a restricted range.

7. A needle and syringe system, comprising:
a syringe assembly that contains a barrel and a plunger, wherein the plunger has a plunger head;
a tubular spacer disposed in said barrel, said spacer having a central opening extending therethrough;
a collar that selectively attaches to said syringe assembly, said collar having a tapered neck and at least one locking protrusion on said tapered neck, wherein said collar supports a needle with a sharpened first end that extends through said tapered neck, and wherein said at least one locking protrusion extends from said tapered neck toward said needle;
a safety slide having a tubular body and a sheathing tube that extends from said tubular body that surrounds part of said needle, said tubular body having a locking groove formed thereon, and wherein said safety slide can move relative to said needle between a first position, where said sheathing tube does not extend beyond said sharpened first end of said needle, and a second position where said sheathing tube extends beyond said sharpened first end of said needle;
wherein said plunger can move in said barrel to contact and move said spacer, wherein said spacer moves said safety slide from said first position to said second position; and wherein said at least one locking protrusion on said tapered neck engages said locking groove on said tubular body as said safety slide moves to said second position, therein locking said safety slide into said second position.

8. The system according to claim 7, wherein said needle is anchored in a needle base and said needle base moves through said central opening in said spacer as said safety slide moves from said first position to said second position.

9. The system according to claim 7, wherein said spacer and said plunger head conform so that no spaces exist between said spacer and said plunger head upon contact between said spacer and said plunger head.

10. The system according to claim 7, further including a visual indicator on said safety slide that becomes visible when said safety slide enters said second position.

11. The system according to claim 7, wherein said barrel mechanically engages said spacer and limits movement of said spacer within said barrel to a restricted range.

12. A method, comprising the steps of:
providing a syringe assembly that contains a barrel and a plunger, wherein the plunger has a plunger head and wherein said barrel has a ring protrusion therein;
positioning a tubular spacer in said barrel, said tubular spacer having a recessed area thereon into which said ring protrusion extends, wherein said ring protrusion in said recessed area limits reciprocal movement of said tubular spacer in said barrel, and wherein said spacer has a central opening extending therethrough;
attaching a needle head to said syringe assembly, wherein said needle head supports a needle with a sharpened first end;
providing a safety slide having a sheathing tube that surrounds part of said needle, and wherein said safety slide can move relative to said needle between a first position, where said sheathing tube does not extend beyond said sharpened first end of said needle, and a second position where said sheathing tube extends beyond said sharpened first end of said needle;
advancing said plunger in said barrel during an injection until said plunger head contacts and moves said tubular spacer, wherein said tubular spacer moves said safety slide from said first position to said second position.

13. The method according to claim 12, wherein said needle is anchored in a needle base and said needle base is moved through said central opening in said tubular spacer as said safety slide moves from said first position to said second position.

14. The method according to claim 12, wherein said tubular spacer and said plunger head conform so that no spaces exist between said tubular spacer and said plunger head when said tubular spacer contacts said plunger head.

15. The method according to claim 12, further including locking said safety slide into said second position as said safety slide enters said second position.

16. The method according to claim 12, further including providing a visual indicator on said safety slide that becomes visible when said safety slide enters said second position.

* * * * *

UNITED STATES PATENT AND TRADEMARK OFFICE
CERTIFICATE OF CORRECTION

PATENT NO. : 10,980,950 B2
APPLICATION NO. : 16/660796
DATED : April 20, 2021
INVENTOR(S) : Barry Berler et al.

It is certified that error appears in the above-identified patent and that said Letters Patent is hereby corrected as shown below:

On the Title Page

At item (71), please amend Applicant to Sharps Technology, Inc., Melville, NY (US).

At item (73), please amend Assignee to Sharps Technology, Inc., Melville, NY (US).

Signed and Sealed this
Nineteenth Day of July, 2022

Katherine Kelly Vidal
*Director of the United States Patent and Trademark Office*